United States Patent [19]

Ciszewski et al.

[11] Patent Number: 4,545,956
[45] Date of Patent: Oct. 8, 1985

[54] METHOD AND APPARATUS FOR DISINFECTING WATERLINES OF A MEDICAL DEVICE

[75] Inventors: Hans-Joachim Ciszewski, Einhausen; Josef Pabst, Heddesheim; Hans-Joerg Weisser, Bensheim, all of Fed. Rep. of Germany

[73] Assignee: Siemens Aktiengesellschaft, Berlin & Munich, Fed. Rep. of Germany

[21] Appl. No.: 558,467

[22] Filed: Dec. 6, 1983

[30] Foreign Application Priority Data

Dec. 14, 1982 [DE] Fed. Rep. of Germany ....... 3246266

[51] Int. Cl.$^4$ .............................................. C02F 1/50
[52] U.S. Cl. ..................... 422/28; 210/764; 210/85; 210/96.1; 210/138; 210/143; 422/116
[58] Field of Search .................. 210/764, 85, 88, 89, 210/96.1, 98, 102, 134, 135, 138–143, 198.1, 205; 422/28, 116

[56] References Cited

U.S. PATENT DOCUMENTS 3,481,689  12/1969  Rosdahl et al. ...................... 422/28
4,078,943   3/1978  Saurenman ........................... 422/28
4,261,950   4/1981  Bainbridge et al. ................. 422/28

FOREIGN PATENT DOCUMENTS 3028550  2/1982  Fed. Rep. of Germany .

*Primary Examiner*—Ivars Cintins
*Attorney, Agent, or Firm*—Hill, Van Santen, Steadman & Simpson

[57] ABSTRACT

A method and apparatus for providing a disinfectant cycle of a medical device such as a dental device having an input water line with a main valve and a plurality of water lines extending to instruments with control valves characterized by an arrangement for injecting a disinfectant into the input line downstream of the main valve and an arrangement for controlling the opening and closing of the various valves to enable replacing the water in the water lines with disinfectant, and subsequently flushing the disinfectant therefrom. The method and apparatus can include a device for dosing the water flowing through the water lines during usage with a disinfectant to retard growth of microorganisms and the apparatus can include a selector switch to select various modes of operation.

15 Claims, 2 Drawing Figures

METHOD AND APPARATUS FOR DISINFECTING WATERLINES OF A MEDICAL DEVICE

BACKGROUND OF THE INVENTION

This invention is directed to a method and apparatus for disinfecting water lines in a medical device or apparatus by shutting off the water, replacing the water in various water lines with a disinfectant and subsequently replacing the disinfectant with fresh water.

Many medical apparatuses, particularly dental apparatuses, have a multitude of water lines which extend branch-like to various individual locations which may be a water faucet or water discharge lines in various instruments or tools. One problem is the elimination of germs or bacteria and the prevention of such microorganisms in the network of various water lines. The growth of these microorganisms is particularly promoted due to the various conditions such as a relatively slight amount of flow of the water, standing times that are relatively long and a temperature range which is conducive to the growth.

For the sterilization of water in medical and/or dental devices, it is known to periodically introduce sterilization fluids into the lines leading to the particular water line outlets by means of a metering pump controlled as a function of the water withdrawal. An example of this is disclosed in German OS No. 30 28 550. When the water has a high contamination or bacteria count, a reduction of the bacteria counts to values required for drinking water quality is possible only after a long period of withdrawing water from the system or not at all because of the problematic nature of the employment of the high disinfectant concentrations.

SUMMARY OF THE INVENTION

The present invention is directed to a method and apparatus wherein the employment of disinfectants can be entirely foregone over a certain time span or wherein smaller amounts will suffice in order to maintain the required water quality. To obtain these objects, the present invention is directed to a method for disinfecting water lines of a medical apparatus such as a dental apparatus, which apparatus has a plurality of water lines with individual control valves and a water supply with a main shutoff valve. The method comprises the steps of shutting the main valve in the water supply, then opening the individual control valves in the water lines to drain the water line and to enable filling and replacing the water lines with disinfectant, after filling the water lines with disinfectant, maintaining the disinfectant in the water lines by closing the various control valves and subsequently after a given prescribed period of time, flushing the water lines by opening the control valves and the main valve in the water supply.

In order to relieve the professional staff, necessary controls are assumed by, for example, providing a means for controlling the sequence and duration of each of the steps such as providing a control means such as a microprocessor or other comparable devices. In addition, the apparatus includes a source of disinfectant with a control disinfectant valve which is connected to the input line downstream of the main shutoff valve and has means to supply disinfectant under pressure. The control means can receive input signals either manually to initiate the program from a clock mechanism to start the program after a given lapse time. In addition, the control means may receive a start signal from a means for determining the bacteria level in the water lines which will initiate a start signal when a given level is received. The control means can function automatically or provide an indication light so that the operator of the apparatus can initiate the disinfecting cycle. It is also possible for the apparatus to not only disinfect but also meter in a small amount of disinfectant as fluid is passed through the dental or medical apparatus and a device can have a selecting switch which enables selecting various modes of disinfecting.

A particularly effective sanitation of the water lines is attained when utilizing a disinfectant such as chlorhexidine digluconate in a concentration between 0.05 and 0.2% in a water solution. An amount between 5 ppm and 1 ppm of this disinfectant can be added to the water by means of a metering device in order to effectively prevent new bacteria growth after an overall disinfection according to the above described method. As an alternative thereto, it is proposed that the water be dosed with a silver preparation like silver sulphate ($Ag_2SO_4$) in a water solution, in an amount of 0.05 through 0.1 mg/liter after the disinfectant with the chlorhexidine digluconate.

DESCRIPTION OF THE PREFERRED EMBODIMENTS

Figure 1:
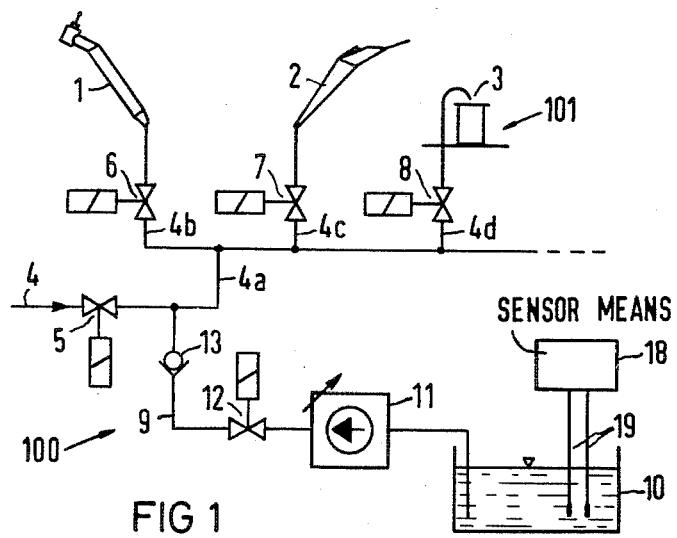
FIG. 1 schematically illustrates a hydraulic plan of the disinfecting apparatus in accordance with the present invention used with a dental apparatus.

The principles of the present invention are particularly useful in an apparatus generally indicated 100 for disinfecting water lines such as 4a, 4b, 4c and 4d of a medical apparatus generally indicated at 101 as a dental apparatus.

As illustrated in the Figure, the dental apparatus 101 has three water discharge or user stations which are illustrated as instruments such as a dental handpiece 1 and a spray handpiece 2, and also a filling means for a glass or cup such as a fountain or faucet 3. Fresh water from a fresh water main or input 4 is supplied through a first solenoid valve or shutoff valve 5 at the input of the dental apparatus 101. The water after passing through the valve 5 goes into water lines such as 4a–4d wherein the water line such as 4b has a control valve 6, the water line 4c has a control valve 7 and the water line 4d has a control valve 8. The control valves such as 6, 7 and 8 can be solenoid valves or pneumatic or manual control valves and the valves can be disposed either in the apparatus or in the user station themselves as is standard, for example, in the case of the spray handpiece 2.

A metering line 9 discharges into the water line section 4a downstream of the shutoff or main valve 5. Disinfectant from a reservoir 10 can be introduced through the metering line 9 by means of a metering device, for example, a variable flow pump 11. A shutoff valve or disinfectant control valve 12 as well as a check valve 13 are in the line 9. The reservoir 10 contains a disinfectant in a concentration sufficient for long-term disinfection and thus assures a "sanitation" of the line paths for a longer time, for example, two to four weeks. The drive of the metering device enables the operation mode to continuously deliver the disinfectants through the line 9 into the water line 4 or the operation of the metering device can be rigidly prescribed for variably operated pulse ratios so that the metering device can deliver the disinfectant continuously or in response to a clock control.

As described yet in greater detail below, it is possible to add the disinfectant directly into the water lines so that these lines 4a–4d are completely filled with a water dosed with a disinfectant to promote a continuous sanitizing mode with the metering device continuously working. A mixture of 5 ppm disinfectant to water is obtained when the concentration of the disinfectant is 0.05% and the ratio of the disinfectant to water consumption is 1:100.

In order to monitor the disinfectant or determine when the employment of different concentrations of disinfectants for "sanitation" and/or "continuously metering" is required and cannot be achieved by means of the aforementioned matching of the conveying capacity of the metering device to the water consumption, sensing means 18 for determining the concentration can detect and report an incorrect concentration of the disinfectant. The sensor means 18 is provided with a pair of electrodes 19 that extend into the reservoir and measure the concentration of the disinfectant. The electrodes 19 also detect and report when the disinfectant reaches a low level and must be refilled.

As mentioned, the device 100 can be operated in a "sanitized" mode or in a continuous metering mode.

The method sequence for long-term disinfectants, i.e., for sanitation of the water lines, is described below given already existing germ infestation. First, the solenoid valve 5 is closed so that the water supply from the water main is interrupted. Then, the control valves allocated to the individual stations such as the valves 6–8 are subsequently opened. The metering device 11 is then switched on. This will introduce disinfectant from the reservoir 10 into the water lines 4a–4d after the solenoid valves 12 of the line 9 has been opened. This operation is expediently controlled by a timing element which is designed so that the disinfectant is supplied until it emerges at the respective exit locations so that all of the water previously contained in the water lines has been rinsed or forced therefrom. During this filling operation, the two instruments such as the dental handpiece 1 and the spray handpiece 2 should expediently be placed in a collecting vessel. Different filling times will occur because of the volume of the network of the water lines and of the conveying capacity of the metering pump. After filling, the control valves such as 6, 7 and 8 for each of the user stations are closed. The disinfectant now is allowed to sit in water line networks for a certain specific time. This time can be up to 24 hours and is sufficient to enable complete sanitizing of the lines. After this time lapse, the fresh water feed is again turned on by means of opening the solenoid valve 5 and the disinfectant is displaced from the various water lines by opening the control valves 6, 7 and 8. The check valve 13, which is in the line 9, will prevent the fresh water from flowing into the reservoir 10.

Chlorhexidine digluconate has proven particularly advantageous, namely, in the concentration between 0.05 and 0.2% for a long term disinfectant. The described sterilization process can be automatically executed every two to four weeks. As a rule, the employment of disinfectant can be omitted during the intervening time. For the purpose of keeping the water lines free of germs and bacteria, after sanitation of the water lines, however, it would also be conceivable to add an amount of chlorhexidine digluconate between 5 ppm and 1 ppm to the water by means of the metering device 11. Reinfection can thus be effectively prevented. A silver preparation like silver sulphate ($Ag_2SO_4$) in a water solution, can also be utilized instead of the chlorhexidine. In this case, the dosing lies between 0.05 and 0.1 mg/liter.

Figure 2:
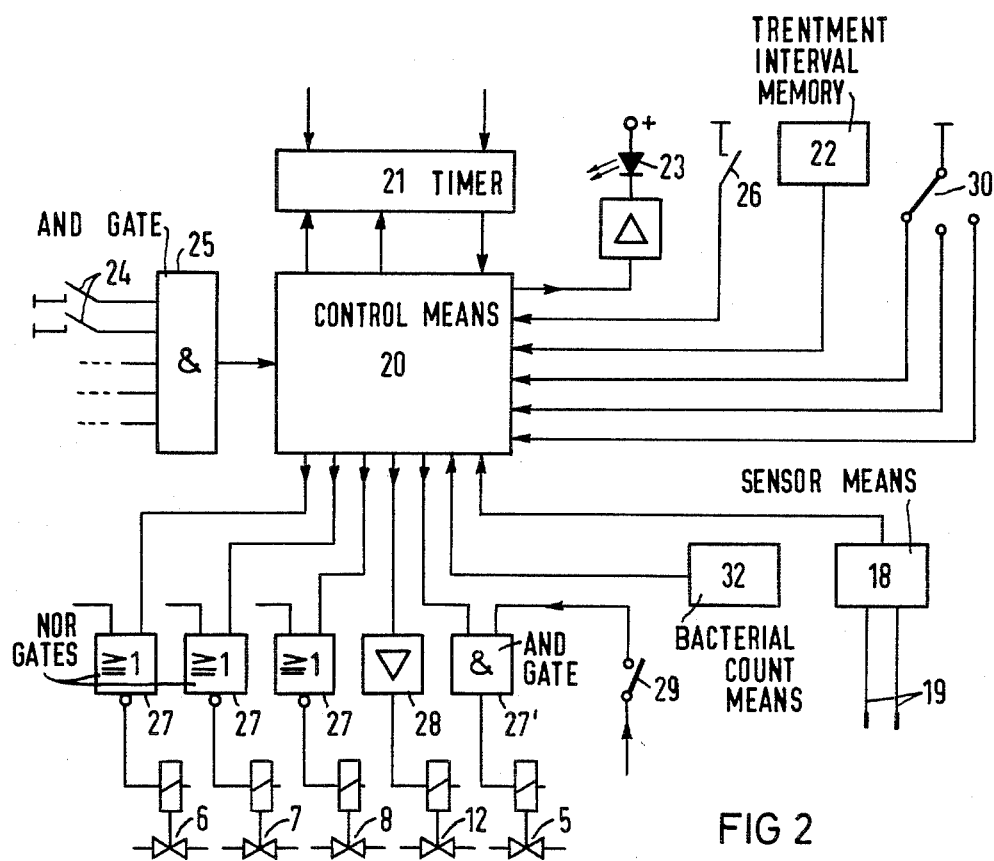
FIG. 2 is a block diagram illustrating the control means for implementing the method according to a given sequence.

As explained in greater detail with reference to FIG. 2, the overall control of the method sequence can expediently occur by utilizing a control means 20 such as a microprocessor having a controlled timing element 21 that is initiated by means of pressing a key or start button. The sequencing of the inventive method will be described with reference to FIG. 2. The central element of sequencing control means 20 is a microprocessor which as explained in yet greater detail below processes the incoming signals and supplies signals for switching the various solenoid valves or supply display signals. The programming of filling times, the sanitation times and the rinse time and the time at which a repeat "sanitation" is necessary which is usually two to four weeks will occur and a timer 21 or, respectively, a treatment interval memory 22 which are separately illustrated to facilitate understanding but which can also be contained within the microprocessor. In one embodiment of the invention, when the interval is over and disinfection of the apparatus is required, a flashing signal will be emitted such as by a light-emitting diode 23 which receives its input from the means 20.

As already described above, the user must remove the handpieces such as 1 and 2 that are usually stored in handpiece supports and expediently these handpieces are then placed in a vessel in order to collect the fluids which are discharged during the disinfecting process. Upon removal of the handpiece from the handpiece supports, signals are forwarded to an "AND" gate operation 25 from signal generators 24 that are provided for each of the handpiece supports. The sequencing control means 20 will receive an H signal only when all of the handpieces have been removed and is thus prepared for starting the method steps already described. When the disinfectant key 26 is now pressed, the method sequence is initiated with the coil of the solenoid valve 5 being switched to shut off the valve, the coils of the valves 6–8 are subsequently switched to open the valves and the coil of the valve 12 is subsequently excited and at the same time the pump of the metering device 11 is switched on. Disinfectant is now pumped from the reservoir 10 into the individual line sections such as 4a–4d. The solenoid valves 6–8 are advantageously successively opened in order to take the various line resistances into consideration. The control means 20 can insure this particular sequence. The drive of the solenoid valve coils occurs through a logic element such as NOR gates 27, AND gate 27' and an amplifier 28. A main switch 29 of the device must be previously switched on.

After completion of the time lapse for disinfection, the main water valve 5 is reopened and the various control valves such as 6–8 are opened. In this condition, the water will flush out the disinfecting fluid.

As mentioned hereinabove, the apparatus 100 can be operated to "disinfect" or sanitize the water lines and also to supply continuous dosing during the time between the sanitizing steps. Thus, the apparatus can be provided with means 30 for selecting the mode. As illustrated, the means 30 for selecting a mode enable selecting a long-term disinfecting mode, a continuous dosing mode or a combination of both. When selecting the long-term sanitation or disinfecting mode, the indicator lamp 23 will indicate when such an operation is necessary.

The control system which is composed of the means or microprocessor 20 plus the timer 21 and the treatment interval memory 22 can be programmed to determine if there is a long pause in the operation of the apparatus 101. If such a long pause which would occur during a vacation is determined, the system can create a signal to indicate that a new sanitation is necessary before resumption of the operation of the apparatus 101.

As mentioned hereinabove, the sensor means 18 which indicates the concentration extends into the reservoir 10 with its electrodes 19 and not only measures the concentration of the disinfectant but also detects and reports when the disinfectant must be refilled. A corresponding interruptive or stop signal concerning the concentration is forwarded to the microprocessor. On the basis of this information concerning the concentration content of the disinfectant, the microprocessor will then determine whether a continuous dosing or a long-term disinfection is necessary and then determine the dosing duration and/or the time interval for the disinfecting operation. It is also conceivable to connect the concentration indicator 18 to the display light 23 through the microprocessor 20 so that the lamp will light up when the level in the reservoir reaches a low level and the reservoir requires refilling.

As mentioned above, the rinsing of the line sections 4a–4d with fresh water will occur after a dwell or standing time of 12 to 24 hours. This amount of time can be preselected and stored in the timer 21.

If the apparatus 100 is provided with means 32 for automatically counting the bacteria, then the sequencing control means 20 can be informed of the number of germs or bacteria present in the water line network. Thus, the sequencing control means 20 can automatically decide whether a long-term disinfection or sanitation is necessary or whether the continuous dosing can be continued. Given this modification, the above-mentioned means 30 for selecting can be omitted from the device.

Although various minor modifications may be suggested by those versed in the art, it should be understood that we wish to embody within the scope of the patent granted hereon, all such modifications as reasonably and properly come within the scope of our contribution to the art.

I claim:

1. A method for disinfecting water lines of a medical device having a plurality of water lines with individual control valves and a water supply with a main valve, said method comprising the steps of providing a supply of disinfectant in a concentration sufficient for long-term disinfection; shutting the main valve in the water supply to stop the flow of water through the water lines and the individual valves; then opening the individual control valves in the water lines and filling the water lines with the disinfectant from the supply of disinfectant; after filling the water lines with disinfectant closing the control valves to maintain the disinfectant in the lines for a prescribed period of time; and then subsequently flushing the water lines by opening the control valves and the main valve of the water supply to cause a flow of water through the water lines.

2. A method according to claim 1, which includes providing the apparatus with means for controlling the sequence and duration of each of the steps upon activation of the means, and said method includes the step of activating said means.

3. A method according to claim 2, wherein the step of activating comprises providing the apparatus with a timing means for creating a starting signal after a predetermined time lapse.

4. A method according to claim 2, which includes indicating means, said control means having means to energize the indicating means when a disinfecting cycle is required so that a manual switch providing the activating signal can be energized.

5. A method according to claim 2, which includes means for sensing the level of bacteria in the water lines, said means for sensing creating a signal for the control means to provide at least an indication of the need to start the disinfecting cycle.

6. A method according to claim 1, wherein the step of providing a supply provides a disinfectant having a concentration of 0.05–0.2% chlorhexidine digluconate.

7. A method according to claim 1, wherein subsequent to the step of flushing the disinfectant from the water lines, adding a disinfectant dosage to the water to retard growth of microorganisms, said dosage being 1–5 ppm of chlorhexidine digluconate.

8. A method according to claim 1, wherein subsequent to flushing the disinfectant from the water lines, dosing the water flowing through the water lines with a disinfectant comprising a silver preparation in the amount of 0.05–0.1 mg/liter of water to retard growth of microorganisms in said water line.

9. An apparatus for disinfecting water lines of a medical device having a water inlet line with a main valve and a plurality of water lines with individual control valves, said apparatus including a source of disinfectant having a disinfectant control valve and means to supply said disinfectant under pressure, said source being connected to the inlet line downstream of the main valve; and control means for generating a disinfectant sequence of selectively closing the main valve and selectively opening the control valves of the water lines to enable draining the water from the water lines, opening the disinfectant control valve to fill the water lines with disinfectant, then closing the control valves of the water lines to maintain the disinfectant in the lines for a given period of time and subsequently opening the main valve and the control valves of the water lines to flush the disinfectant from the water lines, said control means including timing means to automatically initiate the disinfecting cycle after a given period of time.

10. An apparatus according to claim 9, wherein the medical device has support means for supporting individual instruments having water lines, said support means for supporting including indicating means to determine the absence of the instrument from the support means and wherein the control means require a signal from all of the indicating means to show that all instruments are removed from the support means before enabling initiation of the disinfecting cycle.

11. An apparatus according to claim 9, which includes dosage means for metering a disinfectant continuously into the flow of water through the water lines to retard growth of microorganisms, and said control means include a selecting means to select the mode of operation of disinfecting cycle only, disinfecting cycle plus dosage means, and dosage means alone.

12. An apparatus for disinfecting water lines of a medical device having a water inlet line with a main valve and a plurality of water lines with individual control valves, said apparatus including source of disinfectant having a disinfectant control valve and means to supply said disinfectant under pressure, said source being connected to the inlet line downstream of the main valve; and control means for generating a disinfectant sequence of selectively closing the main valve and selectively opening the control valves of the water lines to enable draining the water lines, opening the disinfectant control valve to fill the water lines with disinfectant, then closing the control valves of the water line to maintain the disinfectant in the lines for a given period of time and subsequently opening the main valve and the control valves of the water lines to flush the disinfectant from the water lines, said control means including a display element and means for detecting a bacterial count and providing an indication on the display element when the count reaches a level requiring a disinfecting cycle to be initiated.

13. An apparatus for disinfecting water lines of a medical device having a water inlet line with a main valve and a plurality of water lines with individual control valves, said apparatus including a source of disinfectant having a disinfectant control valve and means to supply said disinfectant under pressure, said source being connected to the inlet line downstream of the main valve; and control means for generating a disinfectant sequence of selectively closing the main valve and selectively opening the control valves of the water lines to enable draining the water lines, opening the disinfectant control valve to fill the water lines with disinfectant, then closing the control valves of the water line to maintain the disinfectant in the lines for a given period of time and subsequently opening the main valve and the control valves of the water lines to flush the disinfectant from the water lines, said control means including pulse means for providing a signal to indicate a need for a disinfectant cycle after a predetermined interval has lapsed between use of the apparatus.

14. An apparatus for disinfecting water lines of a medical device having a water inlet line with a main valve and a plurality of water lines with individual control valves, said apparatus including a source of disinfectant having a disfectant control valve and means to supply said disinfectant under pressure, said source being connected to the inlet line downstream of the main valve and including a metering means for continuously dosing water flowing through the apparatus with a disinfectant of a predetermined amount; and control means for generating a disinfectant sequence of selectively closing the main valve and selectively opening the control valves of the water lines to enable draining the water lines, opening the disinfectant control valve to fill the water lines with disinfectant from the source, then closing the control valves of the water line to maintain the disinfectant in the lines for a given period of time and subsequently opening the main valve and the control valves of the water lines to flush the disinfectant from the water lines, said control means actuating the metering means.

15. An apparatus for disinfecting water lines of a medical device having a water inlet line with a main valve and a plurality of water lines with individual control valves, said apparatus including a source of disinfectant having a disinfectant control valve and means to supply said disinfectant under pressure, said source being connected to the inlet line downstream of the main valve, said source including a reservoir having sensor means for determining the level of the disinfectant in said reservoir, said sensor means also determining the concentration of the disinfectant in the reservoir; and control means for generating a disinfectant sequence of selectively closing the main valve and selectively opening the control valves of the water lines to enable draining the water from the water lines, opening the disinfectant control valve to fill the water lines with disinfectant, then closing the control valves of the water line to maintain the disinfectant in the lines for a given period of time and subsequently opening the main valve and the control valves of the water lines to flush the disinfectant from the water lines.

* * * * *